US008160836B2

(12) United States Patent
Pompei et al.

(10) Patent No.: US 8,160,836 B2
(45) Date of Patent: Apr. 17, 2012

(54) WIRELESS TRANSMISSION OF TEMPERATURE DATA FOR A GEOGRAPHIC AREA

(75) Inventors: Francesco Pompei, Boston, MA (US); Janette H. Lee, Everett, MA (US); Jason N. Jarboe, Somerville, MA (US)

(73) Assignee: Exergen Corporation, Watertown, MA (US)

( * ) Notice: Subject to any disclaimer, the term of this patent is extended or adjusted under 35 U.S.C. 154(b) by 0 days.

(21) Appl. No.: 11/787,651

(22) Filed: Apr. 17, 2007

(65) Prior Publication Data

US 2008/0262782 A1    Oct. 23, 2008

(51) Int. Cl.
*G01K 1/02*    (2006.01)
*G01K 3/06*    (2006.01)
*G06F 3/00*    (2006.01)
*G06F 3/01*    (2006.01)

(52) U.S. Cl. ......... 702/131; 702/130; 702/179; 702/182
(58) Field of Classification Search .......... 702/19, 702/32, 130, 182, 183, 186; 600/300, 549, 600/315; 705/64; 455/67.11
See application file for complete search history.

(56) References Cited

U.S. PATENT DOCUMENTS

| | | | | |
|---|---|---|---|---|
| 6,238,337 B1 * | 5/2001 | Kambhatla et al. | ........... | 600/300 |
| 6,292,685 B1 * | 9/2001 | Pompei | ........... | 600/474 |
| 6,754,470 B2 * | 6/2004 | Hendrickson et al. | ..... | 455/67.11 |
| 6,821,249 B2 * | 11/2004 | Casscells et al. | ........... | 600/300 |
| 7,340,438 B2 * | 3/2008 | Nordman et al. | ........... | 705/64 |
| 2003/0129578 A1 * | 7/2003 | Mault | ........... | 435/4 |
| 2004/0242976 A1 * | 12/2004 | Abreu | ........... | 600/315 |
| 2005/0245839 A1 * | 11/2005 | Stivoric et al. | ........... | 600/549 |

FOREIGN PATENT DOCUMENTS

WO    WO 2008/130535 A1    10/2008

OTHER PUBLICATIONS

Ettore Majorana Foundation and Centre for Scientific Culture, Erice International Seminars on Planetary Emergencies 34th Session, Permanent Monitoring Panel on Terrorism (PMPT) Fourth Meeting, Erice, May 18-22, 2006, Final Report, pp. 1-102.
Shaw, J., "The SARS Scare," *Harvard Magazine* , pp. 48-95 (2007).

(Continued)

*Primary Examiner* — Mohamed Charioui
*Assistant Examiner* — Felix E Suarez
(74) *Attorney, Agent, or Firm* — Hamilton, Brook, Smith & Reynolds, P.C.

(57) ABSTRACT

A user obtains an individual's body temperature data and transmits the data to a medical monitor (e.g., a medical device) for display. Additional data includes a timestamp and location of the body temperature data. Once the data is transmitted, a user may view the medical monitor for a temperature reading. For example, a doctor may take a patient's temperature and the temperature reading is displayed on a medical monitor. The body temperature data of each patient is detected using a preferred temperature detector, such as a temporal artery thermometer using an arterial heat balance approach. After collecting an individual's body temperature data, the body temperature data can be transferred to a processor. By sending body temperature data for many individuals for a geographic region, the processor can identify a pattern (e.g., a pandemic) in the body temperature data.

28 Claims, 8 Drawing Sheets

OTHER PUBLICATIONS

Moore, A., et al., "Summary of Biosurveillance-relevant technologies," School of Computer Science, Carnegie Mellon University and Center for Biomedical Informatics, pp. 1-15.

Moore, A., "Detection Algorithms for Biosurveillance: A tutorial," www.autolab.org, 60 pages.

Henning, Kelly J., "Overview of Syndromic Surveillance, What is Syndromic Surveillance?", www.cdc.gov, 9 pages, retrieved from Internet, Oct. 1, 2007.

EARS V4.5 User Guide, pp. 3-6, Sep. 19, 2006.

HQInc. Wireless Sensing Systems & Designs, CorTemp™ Pill, www.hqinc.net, retrieved from Internet, May 10, 2007.

Notification of Transmittal of the International Search Report for Int'l Appl. No. PCT/US08/04841; Date of Mailing: Sep. 17, 2008.

The Written Opinion of the International Searching Authority for Int'l Appl. No. PCT/US08/04841; Date of Mailing: Sep. 17, 2008.

Notification Concerning Transmittal of International Preliminary Report on Patentability for Int'l Appl. No. PCT/US08/04841; Date of Mailing: Oct. 29, 2009.

* cited by examiner

WIRELESS TRANSMISSION OF TEMPERATURE DATA FOR A GEOGRAPHIC AREA

BACKGROUND OF THE INVENTION

In recent years, thermometers have been used in connection with medical monitors. For example, in 1994 a BCI ear thermometer was introduced by BioChem International using RS-232 to communicate with a monitor. Similarly, in 1996 DATASCOPE™ introduced an infrared ear thermometer having an infrared LED for the wireless transmission of the acquired temperature reading to the patient monitor. This thermometer was designed for use as a stand alone temperature measuring device or to be used with medical monitors via an serial or asynchronous serial connection. In 1996, the temporal artery thermometer was introduced in the form of the LTXA. The LTXA is an infrared temporal artery thermometer using an RS-232 cable data link for data transmission. The Temporal Artery thermometer may also be used with medical monitors.

For example, FIG. 2 shows a way of collecting and transmitting temperature data that includes a body portion 205, a temperature detector 210, a communications path 215, and a medical device 220. In one embodiment, a cradle 225 may be used to store the temperature detector 210. In use, the temperature detector 210 obtains a temperature reading from a body portion 205 and sends the temperature reading to the medical device 220 for display. In particular embodiments, the temperature detector 210 uses an RS-232 output and transmits the temperature reading to the medical device 220.

In this example embodiment, the temperature detector 210 obtains body temperature data from the body portion 205. With the body temperature data, an internal core temperature can be computed using an arterial heat balance. The teachings of calculating body temperature data is described in U.S. Pat. No. 6,292,685, which is hereby incorporated by reference. It is useful to note that embodiments of the present invention are not limited to temporal artery readings. Instead, any type of temperature detector may be used, including axillary, ear, or non-radiation detectors. Moreover, the medical device 220, instead of the temperature detector 210, may also calculate the temperature reading upon receiving the raw temperature data such as heat flux and ambient temperature data. One such example is shown in FIG. 1.

In particular, FIG. 1 illustrates the temporal arteries 12 and 14 that extend upwardly toward the side of the human face and bifurcate at 16 and 18 in the forehead region. In that region, the temporal artery passes over the skull bone very close to the skin and is thus termed the superficial temporal artery. The superficial temporal artery is, therefore, particularly accessible for providing temperature readings and, as an artery, has a temperature close to the heart temperature. Further, there are no known arterial/venus anastomoses, that is, shunts between the artery and veins for regulation of skin temperature. Accordingly, the blood flow is relatively stable, varying a maximum of only 50% as opposed to as much as 500% in other areas of the skin.

To locate the temporal artery, a temperature sensor, preferably a radiation detector 20, is scanned across the side of the forehead over the temporal artery while electronics in the detector search for the peak reading which indicates the temporal artery. Preferably, that temperature reading is then further processed in accordance with an algorithm specific to the temporal artery for providing a display temperature which may, for example, correspond to core, oral or rectal temperature.

SUMMARY OF THE INVENTION

By sending body temperature data for many individuals, preferably over geographic regions, the processor can identify a pattern (e.g., a pandemic) in the body temperature data.

In an example embodiment a pattern is determined for body temperature data of multiple individuals. More accurately, a process detects body temperature data of a plurality of individuals and transmits the body temperature data over a wireless communications path to a processor. The processor also receives or determines a timestamp and location for the body temperature data. Analyzing the data, the processor determines a pattern in the body temperature data. For convenience, the processor stores the body temperature data in a database, determines a pattern (e.g., an epidemic, pandemic, or an outbreak in an identified geographic location), and displays the pattern to a user of the processor.

In one convenient implementation, a transmitter sends body temperature data using a Subscriber Identity Module (SIM) card or General Packet Radio Service (GPRS) to send a Short Message Service (SMS), text message, or email message to the processor.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

The teachings of all patents, published applications and references cited herein are incorporated by reference in their entirety.

Figure 1:
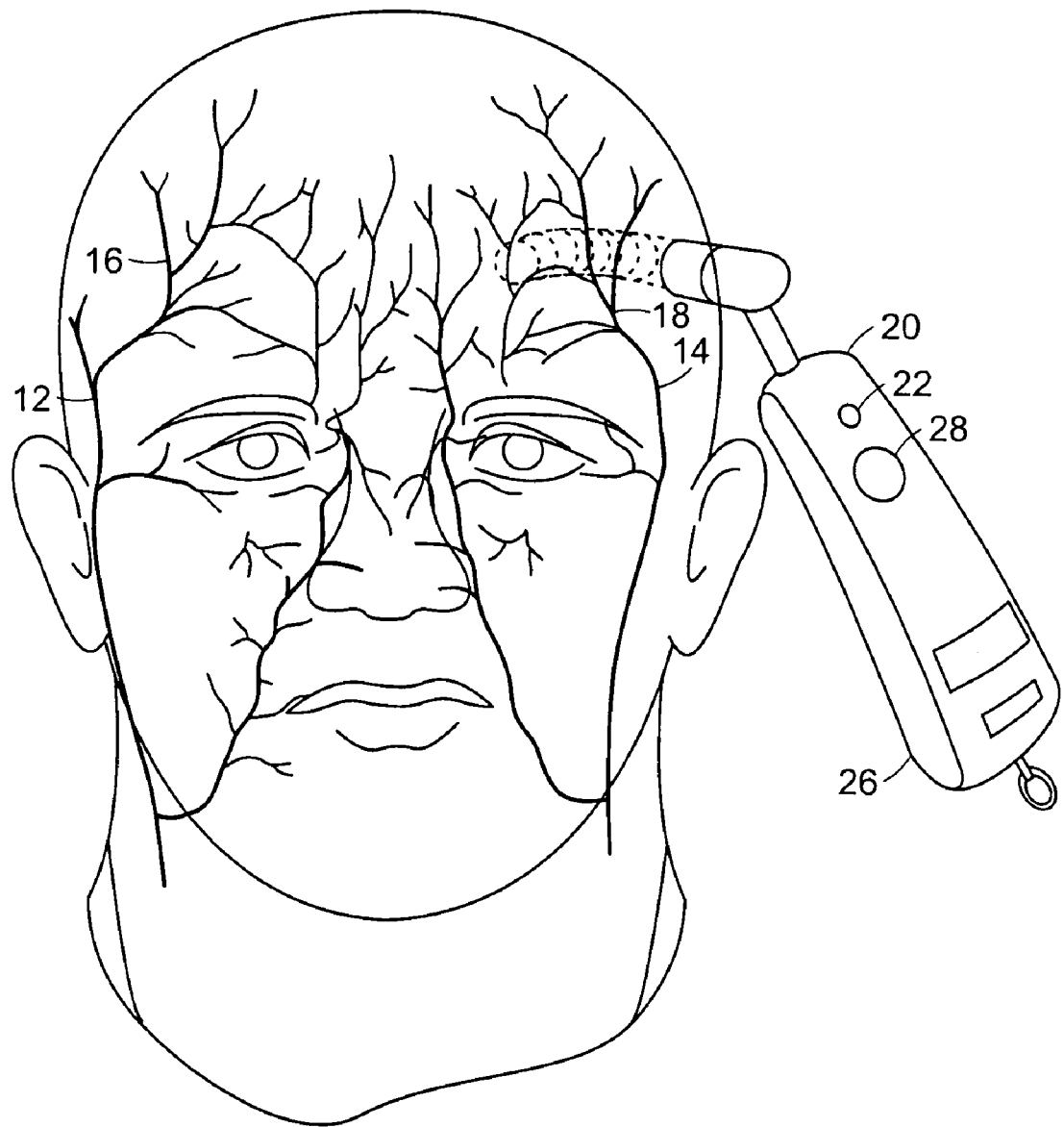
FIG. 1 illustrates an infrared thermometer scanning the temporal artery.
Figure 2:
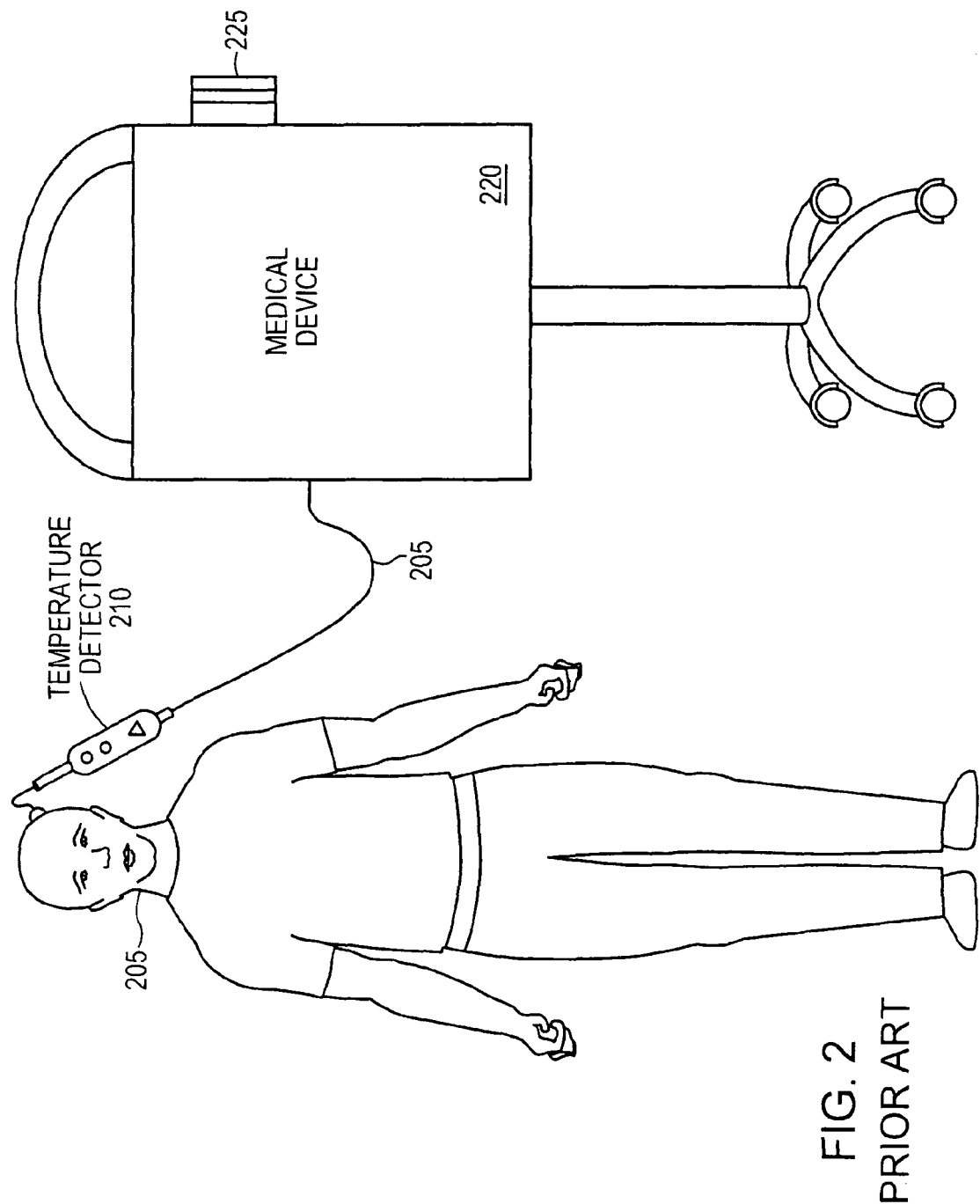
FIG. 2 is a high level view of collecting and transmitting temperature data.
Figure 3:
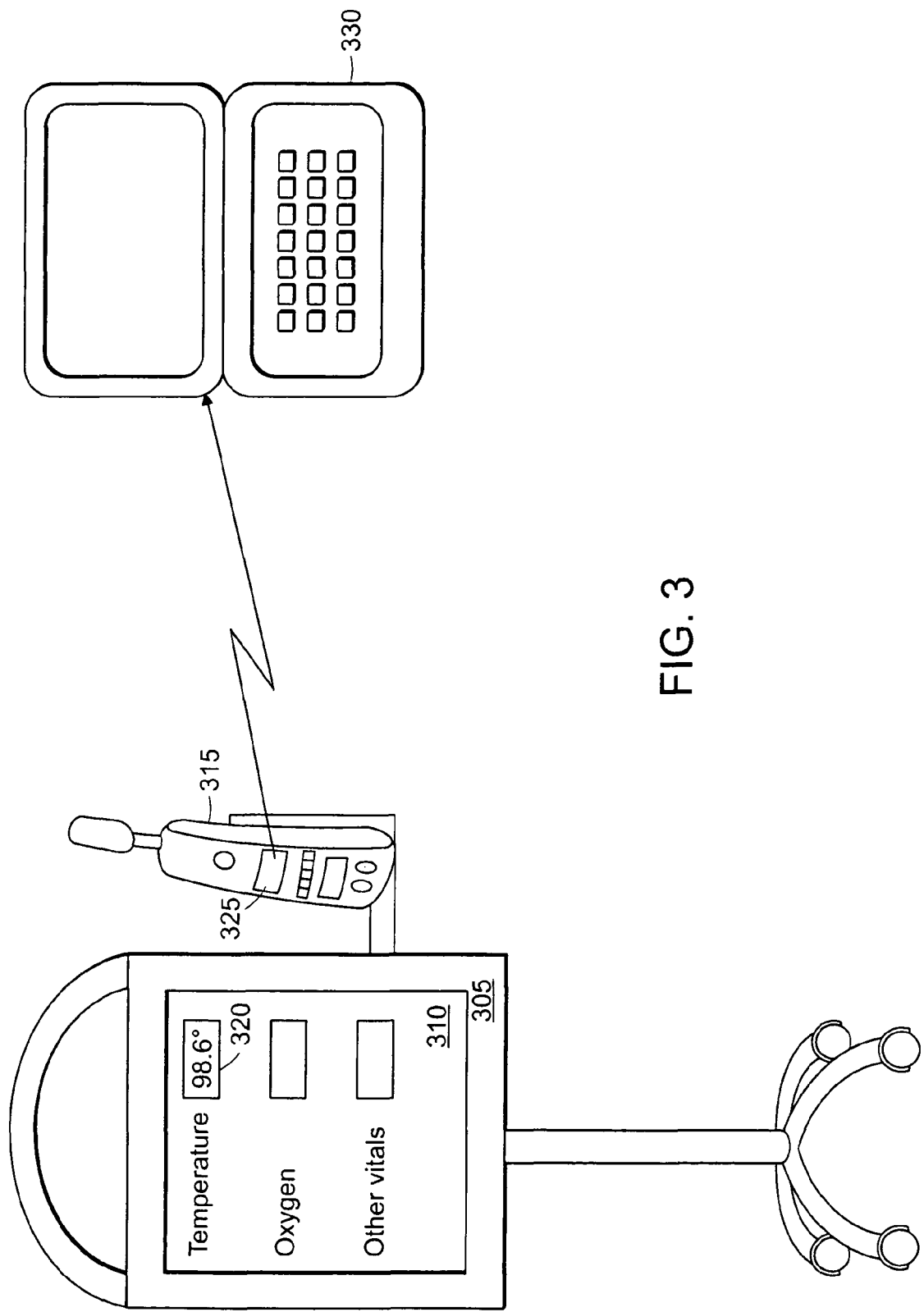
FIG. 3 is a high level view of a medical monitor for displaying and transmitting temperature data.

FIG. 3 is a high level view of a medical device 305 for displaying and transmitting temperature data. The medical device 305 provides a user (e.g., a doctor) multiple attachments, such as a temperature detector 315, blood pressure cuff, and oxygen pulse sensor, for obtaining medical data. The medical monitor 305 displays the medical data on a display screen 310 to allow a user to monitor a patient's medical data. One useful piece of medical data that is collected and displayed is temperature 320. In operation, the temperature detector 315 obtains body temperature data from a body portion and provides the medical device 305 with a temperature reading via a connection, such as RS-232. In a convenient embodiment, the temperature detector 315 includes a wireless module 325 for transmission. For example, the wireless module 325 may be used to transmit the temperature reading from the temperature detector to a processor 330.

The processor 330 may access the temperature data to create a histogram for an aggregate data collection. In particular, data may be used to evaluate screening programs at airports, schools, factories and other populated environments, during perceived potential epidemics for persons who may be at risk for transmitting epidemic diseases. Such evaluations may be aided by the analysis of the data statistically to identify persons with unexpectedly high temperatures, indicating possible fever. Such identified persons would be detained briefly for closer examination by a medically trained person. The data would allow use of mathematical routines which would maximize the sensitivity for detecting sick individuals to prevent the spread of disease, while minimizing false positives, which unnecessarily inconveniences people and adds delay.

Figure 4:
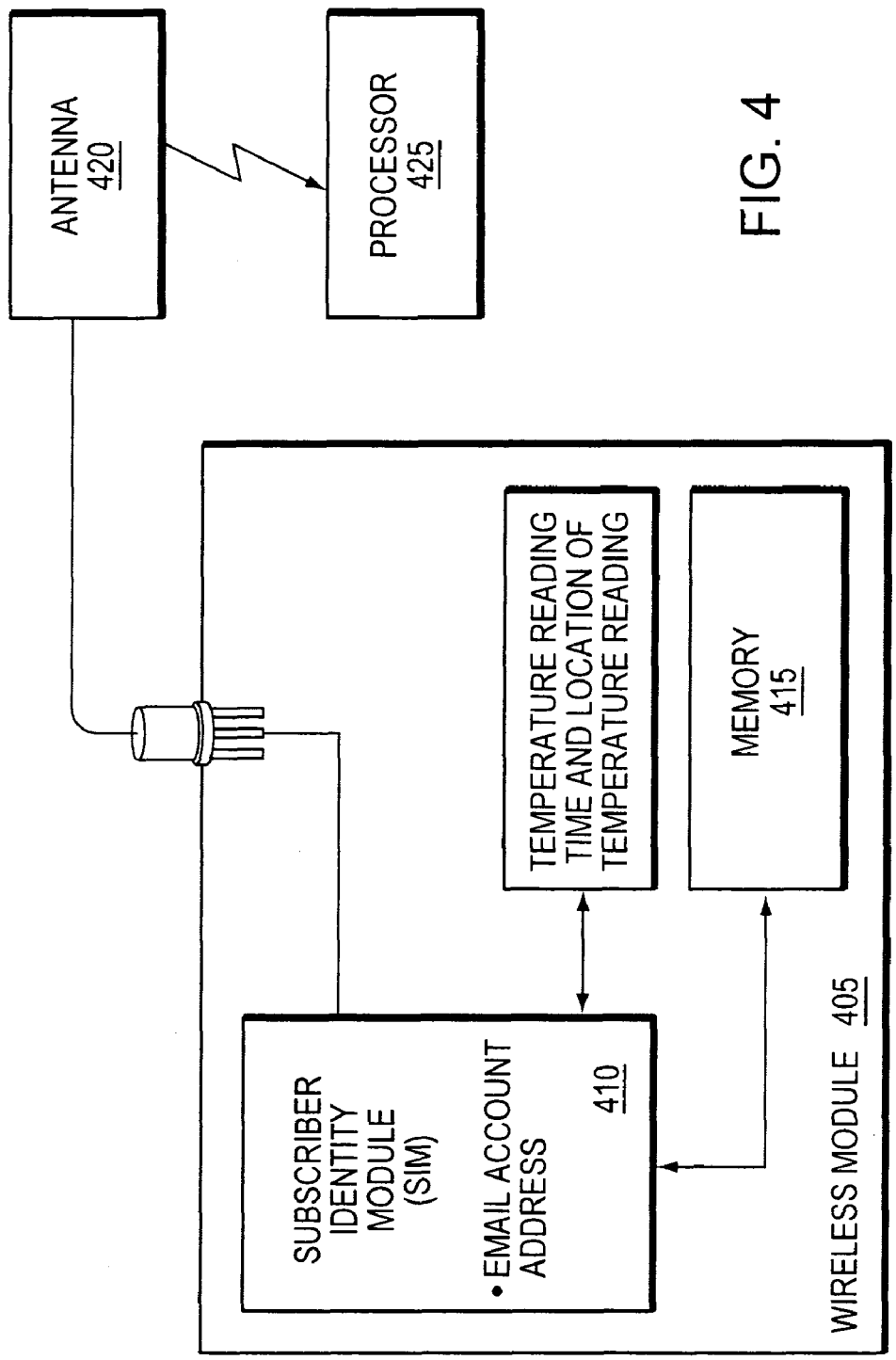
FIG. 4 is a detailed view of a wireless unit transmitting body temperature data.

FIG. 4 shows a wireless module 405 that transmits data from a temperature detector to a processor 425. In one embodiment, the wireless module 405 may be a printed circuit board incorporating the features of a commercial cell phone module. Further, the printed circuit board of the wireless module 405 may be in a plastic wall-mounted enclosure, such as the cradle shown in FIG. 6. In a convenient embodiment, the wall-mounted enclosure serves as a cradle for a temperature detector, such as a temporal artery thermometer. The wireless module 405 may be a tri-band global use including a Subscriber Identity Module (SIM) card 410, memory 415 to store an email address or account information, and an antenna 420. It is useful to note that the wireless module 405 may be operated using battery or AC/DC adapter power.

In operation, the wireless module 405 transmits data via email using the wireless module 405 and SIM card 410. More specifically, the wireless module 405 obtains an email account address stored in the SIM card 410, memory 415, or a microchip within the wireless module 405. The wireless module 405 transmits a temperature reading, the time of the temperature reading, and the location of the temperature reading via an email message to the processor 425 for processing. During transmission, the wireless module 405 may use an antenna 420 that is either external as shown or an on-board antenna. After transmission, the processor processes the data. It is useful to note that the data may be received by a database on the processor 425 instead of an email account. Further, the data may be time stamped by the processor 425 or receiving email account. Likewise, the location of the data may be determined by the processor 425 or receiving email account based on specified information, such as a registration card for the wireless module 405. In a convenient embodiment, the wireless module 405 also includes a real-time clock for time stamping the data and a Global Positioning System (GPS) module to identify location of the data.

In an alternative embodiment, General Packet Radio Service (GPRS) may be used for transmitting data and data is sent over a cell phone network using an authenticated account. GPRS is a mobile data service available to users of Global System for Mobile Communications (GSM) and IS-136 mobile units. GPRS data transfer is typically charged per megabyte of transferred data, while data communication via traditional circuit switching is billed per minute of connection time, independent of whether the user has actually transferred data or he has been in an idle state. GPRS can be utilized for services such as Wireless Application Protocol (WAP) access, and SMS, but also for Internet communication services such as email and web access. GPRS costs are directly proportionate to the amount of data sent. Thus, when sending small amounts of data, GPRS may be more cost effective than using an email account. One additional way to increase cost effectiveness is to transmit a group of temperature readings and associated information in a batch. Using a batch to transmit data, allows fewer packets of data to be transmitted resulting in a cost reduction.

Figure 5:
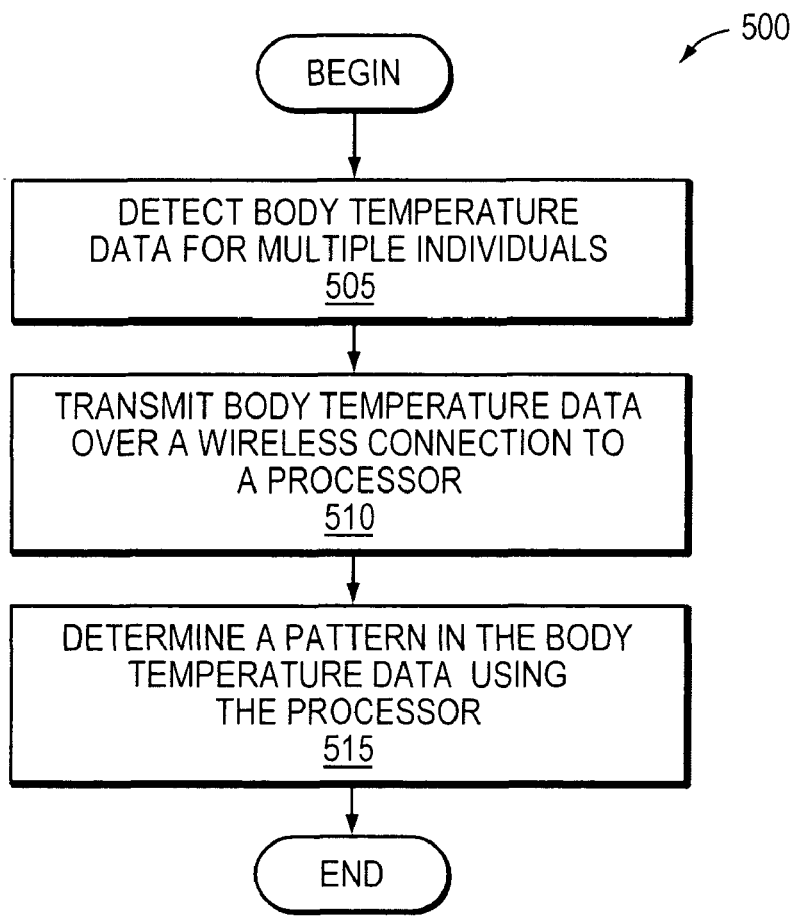
FIG. 5 is a flow diagram illustrating an example temperature reading and wireless transmission process.

FIG. 5 is a flow diagram 500 illustrating an example temperature reading and wireless transmission process. After beginning, the process detects body temperature data for multiple individuals (505). Next, the process transmits the body temperature data over a wireless communications path to a processor (510). After transmitting the body temperature data, the process determines a pattern in the body temperature data using the processor (515). For example, mathematical routines may be applied to the data to identify a pattern and, in turn, indicate a pandemic outbreak in a geographic area.

Patterns may be identified from a control or baseline for an average percentage of fevers per day. Temporal and spatiotemporal data can be used to assess day-to-day and day and place variability of data from an expected baseline. In some cases, about half the baseline data includes an above average temperature. Thus, approaches are used that include standard deviations of data to prevent false positives of an outbreak. One such approach that recognizes false positives is the syndromic surveillance used by the Centers for Disease Control and Prevention (CDC™). The syndromic surveillance, for example, may be used for outbreak detection to identify a signal corresponding to an outbreak or cluster amid substantial "background noise" in the data. Yet another example approach is the Early Aberration Reporting System™ (EARS) created by the CDC™. EARS may be used to identify influenza or other aliments based on data, such as temperature data.

Figure 6:
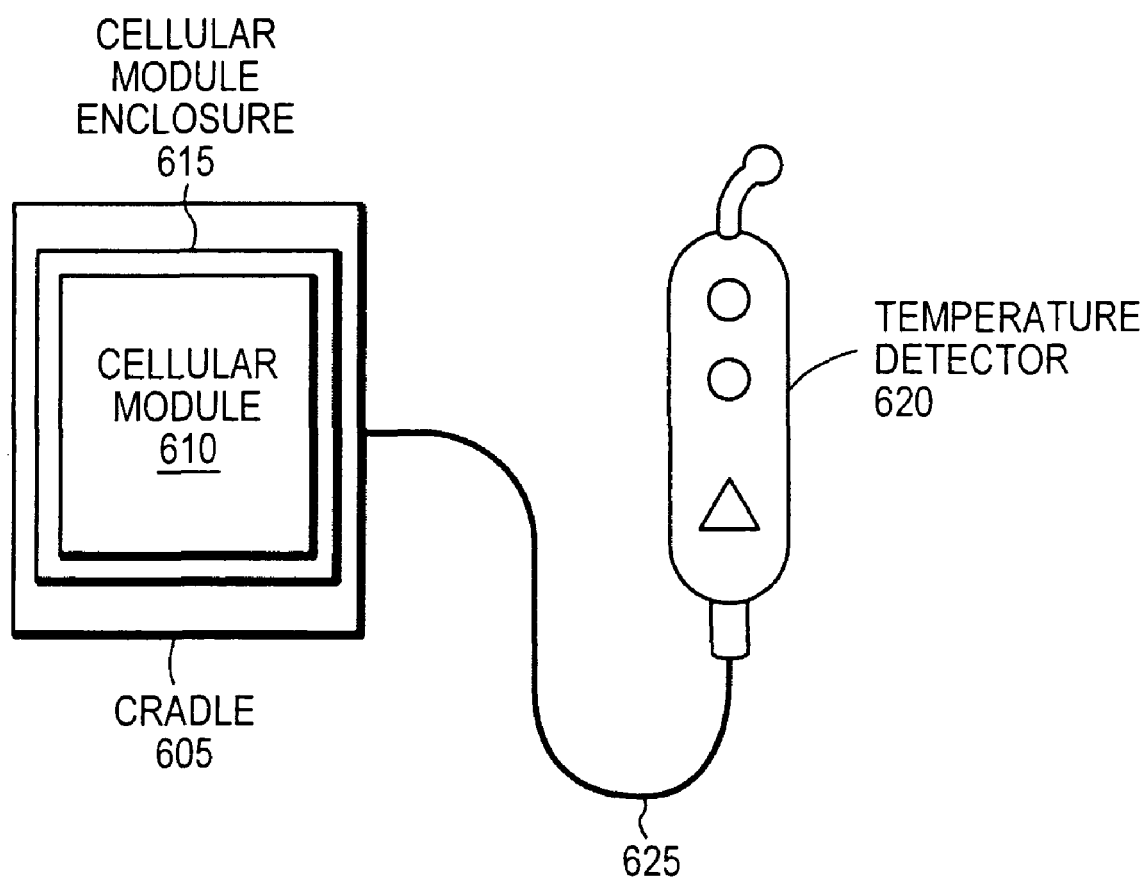
FIG. 6 illustrates a cellular cradle connected to a temperature detector.

In particular embodiments, a cradle is used to enclose a cellular module as shown in FIG. 6. In particular, FIG. 6 shows a cradle 605 that has a cellular module 610 within an enclosure 615. In operation, the cellular module 610 receives data from a temperature detector 620 via a connection 625. After receiving the data, the cellular module 610 transmits the data to a processor. In an embodiment, the temperature detector 620 is also placed in the cradle 605, which does not affect the cellular module 610 transmission of data to the processor.

Figure 7:
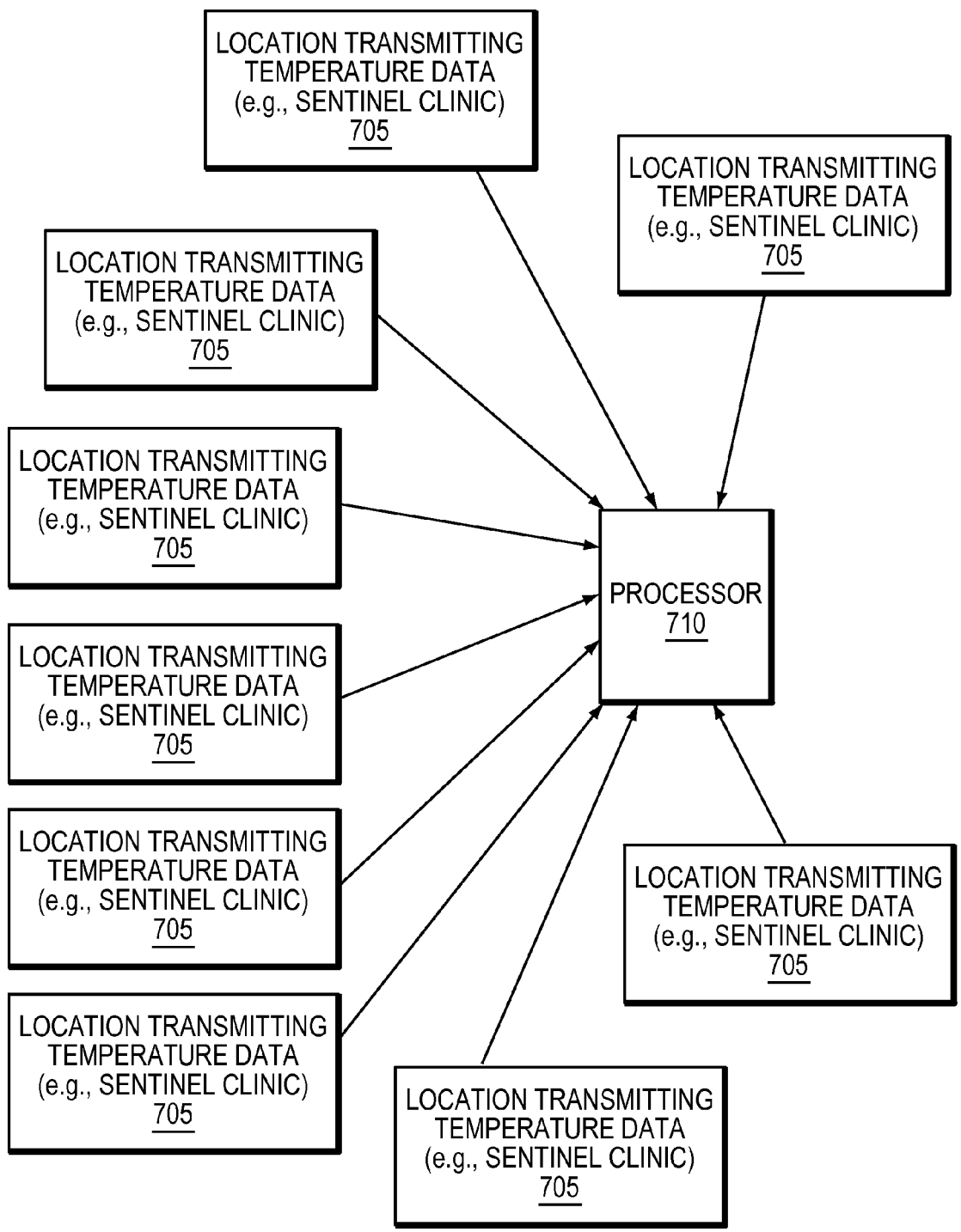
FIG. 7 is a diagram depicting multiple locations communicating with a processor.
Figure 8:
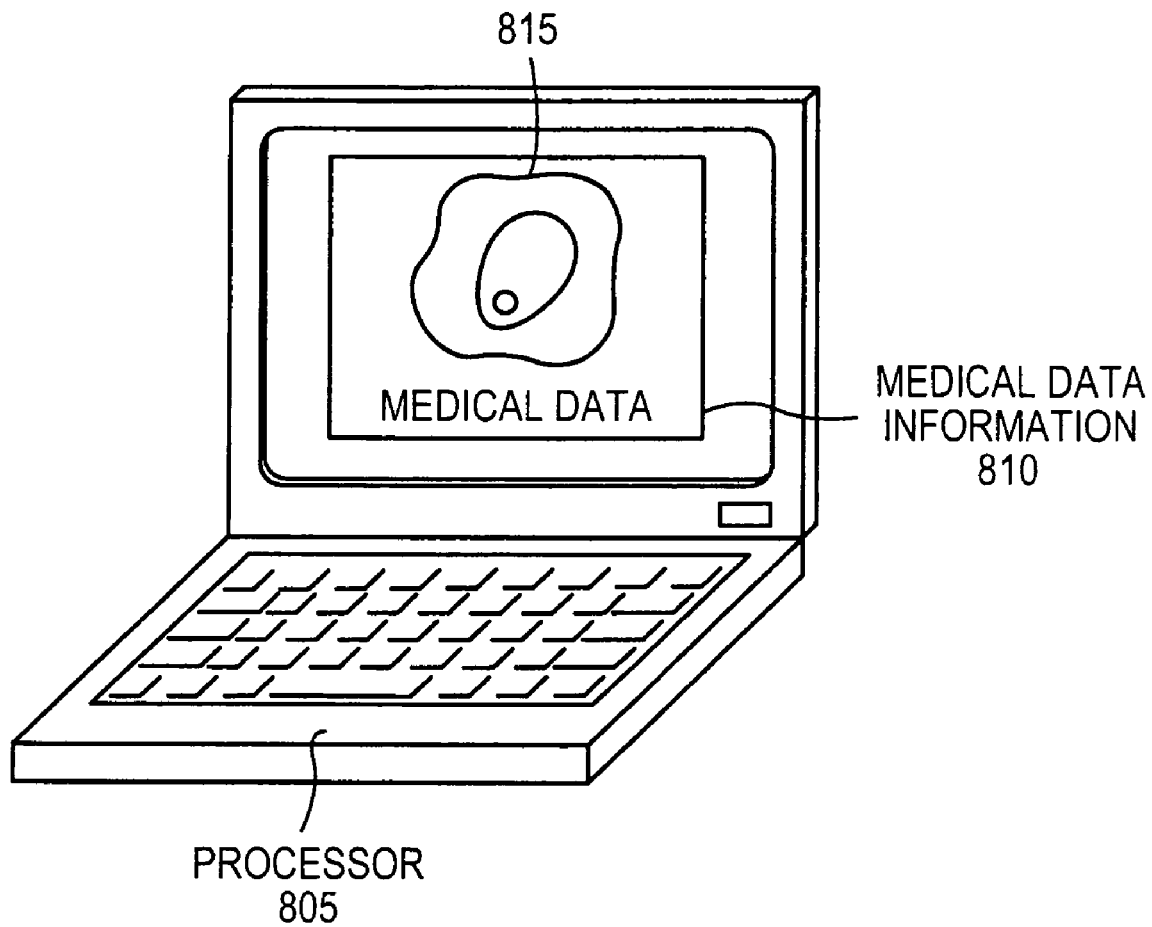
FIG. 8 is a detailed view of a processor displaying pattern information.

A processor may receive data from multiple locations. More specifically, FIG. 7 shows multiple sites 705 sending data to a processor 710. For example, multiple Sentinel clinics may send temperature readings to a central processor. After sending the data to the processor 710, the processor 710 can process the data from each of the multiple sites 705 to identify one or more outbreaks over multiple geographic locations. In some cases an outbreak may be identified in multiple geographic locations. Identifying an outbreak may be done visually by viewing a processor display as shown in FIG. 8. More accurately, FIG. 8 shows a processor 805 displaying medical data information 810 in a useful way. For example, a display band 815 may indicate to a user that an outbreak exists in a geographic location. It is useful to note that indications from multiple bands may indicate an outbreak in multiple geographical locations.

It should be understood that the processes disclosed herein, such as transmitting temperature readings, such as FIG. 5, may be implemented in the form of hardware, firmware, and/or software. If implemented in software, the software may be processor instructions in any suitable software language and stored on any form of computer readable medium.

The processor instructions are loaded and executed by a processor, such as a general purpose or application specific processor, that, in turn, performs the example embodiments disclosed herein.

While this invention has been particularly shown and described with references to example embodiments thereof, it will be understood by those skilled in the art that various changes in form and details may be made therein without departing from the scope of the invention encompassed by the appended claims.

What is claimed is:

1. A method of identifying a pattern in body temperature data, comprising:
   using a common temperature detector to detect body temperature data for a plurality of individuals;
   transmitting from the common temperature detector the body temperature data over a wireless communications path to a processor; and
   determining a pattern in the body temperature data from the plurality of individuals using the processor to indicate a disease outbreak in a geographic area based on a change in percentage of fevers for a time period and using statistical analysis of the temperature data to avoid false positives in indication of the disease outbreak.

2. The method of claim 1 wherein using the common temperature detector to detect body temperature data of a plurality of individuals further comprises scanning across the temporal artery for each individual to obtain body temperature data.

3. The method of claim 1 further comprising storing the body temperature data in a database in the processor.

4. The method of claim 1 wherein transmitting the body temperature data uses a cell phone module.

5. The method of claim 4 wherein the cell phone module includes a Subscriber Identity Module (SIM) card.

6. The method of claim 4 wherein the cell phone module includes a General Packet Radio Service (GPRS).

7. The method of claim 4 wherein the cell phone module transmits in the form of a Short Message Service (SMS), text message, or email message.

8. The method of claim 1 further comprising displaying the pattern to a user of the processor.

9. The method of claim 1 wherein the pattern identifies an epidemic.

10. The method of claim 1 wherein the pattern identifies a pandemic.

11. The method of claim 1 wherein the pattern identifies an outbreak in an identified geographic location.

12. The method of claim 1 further comprising transmitting the body temperature data from multiple locations.

13. The method of claim 1 wherein the pattern identifies an outbreak in multiple geographic locations.

14. A system for identifying a pattern in temperature data, comprising:
   a common temperature detector to detect body temperature data for a plurality of individuals;
   a transmitter associated with the common temperature detector that transmits body temperature data from the common temperature detector over a wireless communications path to a processing unit; and
   the processing unit that determines a pattern in the body temperature data from the plurality of individuals to indicate a disease outbreak in a geographic area based on a change in percentage of fevers for a time period and uses statistical analysis of the temperature data to avoid false positives in indication of the disease outbreak.

15. The system of claim 14 wherein the common temperature detector scans across the temporal artery to obtain body temperature data.

16. The system of claim 14 wherein the processor stores the body temperature data in a database.

17. The system of claim 14 wherein the transmitter is a cell phone module.

18. The system of claim 17 wherein the cell phone module includes Subscriber Identity Module (SIM) card to transmit body temperature data.

19. The system of claim 17 wherein the cell phone module includes a General Packet Radio Service (GPRS) to transmit body temperature data.

20. The system of claim 17 wherein the cell phone module transmits in the form a Short Message Service (SMS), text message, or email message to transmit body temperature data.

21. The system of claim 14 wherein the processing unit displays the pattern to a user of the processing unit.

22. The system of claim 14 wherein the pattern identifies an epidemic.

23. The system of claim 14 wherein the pattern identifies a pandemic.

24. The system of claim 14 wherein the pattern identifies an outbreak in an identified geographic location.

25. The system of claim 14 wherein the pattern is based on the body temperature data from multiple transmitters.

26. The system of claim 14 wherein the pattern identifies an outbreak in multiple geographic locations.

27. A system for identifying a pattern in body temperature data, comprising:
   means for detecting body temperature data for a plurality of individuals, the means for detecting body temperature data being common for the plurality of individuals;
   means for transmitting the body temperature data from the means for detecting body temperature data over a wireless communications path to a processor means; and
   the processor means for determining a pattern in the body temperature data from the plurality of individuals to indicate a disease outbreak in a geographic area based on a change in percentage of fevers for a time period, the processor means using statistical analysis of the temperature data to avoid false positives in indication of the disease outbreak.

28. A system for transmitting temperature data, comprising:
   a common temperature detector that detects body temperature data of a plurality of individuals;
   a cellular transmitter associated with the common temperature detector that transmits body temperature data of the plurality of individuals from the common temperature detector over a wireless communications path to a processing unit; and
   a processor that determines a pattern in body temperature data of the plurality of individuals to indicate a disease outbreak in a geographic area based on a change in percentage of fevers for a time period and uses statistical analysis of the temperature data to avoid false positives in indication of the disease outbreak.

* * * * *